United States Patent
Kahle et al.

(10) Patent No.: US 7,163,510 B2
(45) Date of Patent: Jan. 16, 2007

(54) SURGICAL INSTRUMENT ACCESS DEVICE (75) Inventors: Henry Kahle, Trabuco Canyon, CA (US); Payam Adlparvar, Lake Forest, CA (US); Gary M. Johnson, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 262 days.

(21) Appl. No.: 10/666,579

(22) Filed: Sep. 17, 2003

(65) Prior Publication Data
US 2005/0059865 A1  Mar. 17, 2005

(51) Int. Cl.
*A61B 1/32* (2006.01)

(52) U.S. Cl. .................... 600/208; 604/167.2

(58) Field of Classification Search ........... 600/208, 600/206, 203; 604/167.04, 167.06; 606/108, 606/191, 213
See application file for complete search history.

(56) References Cited

U.S. PATENT DOCUMENTS

| | | |
|---|---|---|
| 1,810,466 A | 6/1931 | Deutsch |
| 2,305,289 A | 12/1942 | Coburg |
| 2,835,253 A | 5/1958 | Borgeson |

(Continued)

FOREIGN PATENT DOCUMENTS

| | | |
|---|---|---|
| IE | S940150 | 2/1994 |
| IE | S940613 | 8/1994 |
| IE | S940960 | 12/1994 |

(Continued)

OTHER PUBLICATIONS

Neil Sheehan, Supplemental Expert Report of Neil Sheehan Re: U.S. Patent No. 5,741,298, dated Aug. 9, 2005, The United States District Court for the Central District of California, Civil Action No. SACV 03-1322 JVS (MLGx).

(Continued)

*Primary Examiner*—Cary E. O'Connor
(74) *Attorney, Agent, or Firm*—David G Majdali; Kenneth K Vu (57) ABSTRACT

A surgical access device includes a single valve that forms a seal with a body wall and provides an access channel into a body cavity. The valve has properties for creating a zero seal in the absence of an instrument as well as an instrument seal for an instrument having a diameter up to about 37 mm. The valve can include a gel material and the access channel can include a protective sleeve to provide for wound protection during insertion and withdrawal of a sharp surgical instrument. The valve further comprises a cap ring which may be inserted or molded with the gel material. The protective sleeve may be bonded or molded around an inner diameter of the cap ring. The protective sleeve may be a single tubular member, or may comprise a plurality of axially extending sleeve members having a plurality of axial slits. The protective sleeve and the cap ring may comprise of the same or different materials. The surgical access device further comprises at least one support ring disposed circumferentially of the valve forming a hollow space, and a wound retractor operatively placed in the hollow space. The wound retractor includes an inner ring, an outer ring, and a flexible sleeve connecting the inner ring and the outer ring.

10 Claims, 9 Drawing Sheets

U.S. PATENT DOCUMENTS

| | | | |
|---|---|---|---|
| 2,853,075 A | 9/1958 | Hoffman et al. | |
| 3,039,468 A | 6/1962 | Price | |
| 3,111,943 A | 11/1963 | Orndorff | |
| 3,244,169 A | 4/1966 | Baxter | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 3,416,520 A | 12/1968 | Creager, Jr. | |
| 3,447,533 A | 6/1969 | Spicer | |
| 3,523,534 A | 8/1970 | Nolan | |
| 3,717,151 A | 2/1973 | Collett | |
| 3,841,332 A | 10/1974 | Treacie | |
| 3,850,172 A | 11/1974 | Cazalis | |
| 3,856,021 A | 12/1974 | McIntosh | |
| 4,024,872 A | 5/1977 | Muldoon | |
| 4,043,328 A | 8/1977 | Cawood, Jr. et al. | |
| 4,083,370 A | 4/1978 | Taylor | |
| 4,188,945 A | 2/1980 | Wenander | |
| 4,217,664 A | 8/1980 | Faso | |
| 4,222,126 A * | 9/1980 | Boretos et al. | 623/2.19 |
| 4,338,937 A | 7/1982 | Lerman | |
| 4,367,728 A | 1/1983 | Mutke | |
| 4,550,713 A | 11/1985 | Hyman | |
| 4,553,537 A | 11/1985 | Rosenberg | |
| 4,755,170 A | 7/1988 | Golden | |
| 4,777,943 A | 10/1988 | Chvapil | |
| 4,863,438 A | 9/1989 | Gauderer et al. | |
| 4,895,565 A * | 1/1990 | Hillstead | 604/167.04 |
| 4,903,710 A | 2/1990 | Jessamine et al. | |
| 4,926,882 A | 5/1990 | Lawrence | |
| 4,950,223 A | 8/1990 | Silvanov | |
| 4,984,564 A | 1/1991 | Yuen | |
| 4,991,593 A | 2/1991 | LeVahn | |
| 4,998,538 A | 3/1991 | Charowsky et al. | |
| 5,015,228 A | 5/1991 | Columbus et al. | |
| 5,037,379 A | 8/1991 | Clayman et al. | |
| 5,178,162 A | 1/1993 | Bose | |
| 5,192,301 A | 3/1993 | Kamiya et al. | |
| 5,213,114 A | 5/1993 | Bailey, Jr. | |
| 5,299,582 A | 4/1994 | Potts | |
| 5,316,541 A | 5/1994 | Fischer | |
| 5,350,364 A | 9/1994 | Stephens | |
| 5,353,786 A | 10/1994 | Wilk | |
| 5,366,478 A | 11/1994 | Brinkerhoff et al. | |
| 5,368,545 A | 11/1994 | Schaller et al. | |
| 5,380,288 A | 1/1995 | Hart | |
| 5,389,080 A | 2/1995 | Yoon | |
| 5,389,081 A | 2/1995 | Castro | |
| 5,407,433 A * | 4/1995 | Loomas | 604/167.06 |
| 5,429,609 A | 7/1995 | Yoon | |
| 5,460,616 A | 10/1995 | Weinsteien | |
| 5,476,475 A | 12/1995 | Gadberry | |
| 5,480,410 A | 1/1996 | Cuschieri et al. | |
| 5,492,304 A | 2/1996 | Smith | |
| 5,496,280 A | 3/1996 | Vandenbroek | |
| 5,503,112 A | 4/1996 | Luhman et al. | |
| 5,514,133 A | 5/1996 | Golub | |
| 5,522,791 A | 6/1996 | Leyva | |
| 5,524,644 A | 6/1996 | Crook | |
| 5,531,758 A | 7/1996 | Uschold | |
| 5,545,179 A | 8/1996 | Williamson, IV | |
| 5,562,677 A | 10/1996 | Hildwein et al. | |
| 5,603,702 A | 2/1997 | Smith | |
| 5,628,732 A * | 5/1997 | Antoon et al. | 604/167.06 |
| 5,634,936 A | 6/1997 | Linden et al. | |
| 5,634,937 A | 6/1997 | Mollenauer et al. | |
| 5,636,645 A | 6/1997 | Ou | |
| 5,640,977 A | 6/1997 | Leahy et al. | |
| 5,653,705 A | 8/1997 | de la Torre et al. | |
| 5,672,168 A | 9/1997 | de la Torre et al. | |
| 5,681,341 A | 10/1997 | Lunsford et al. | |
| 5,709,664 A | 1/1998 | Vandenbroek | |
| 5,720,730 A | 2/1998 | Blake, III | |
| 5,728,103 A | 3/1998 | Picha et al. | |
| 5,741,298 A | 4/1998 | MacLeod | |
| 5,782,817 A | 7/1998 | Franzel | |
| 5,792,119 A | 8/1998 | Marx | |
| 5,795,290 A | 8/1998 | Bridges | |
| 5,803,919 A * | 9/1998 | Hart et al. | 604/167.04 |
| 5,803,921 A | 9/1998 | Bonadio | |
| 5,810,721 A | 9/1998 | Mueller et al. | |
| 5,813,409 A | 9/1998 | Leahy et al. | |
| 5,814,026 A | 9/1998 | Yoon | |
| 5,841,298 A | 11/1998 | Huang | |
| 5,853,395 A | 12/1998 | Crook et al. | |
| 5,865,729 A | 2/1999 | Meehan et al. | |
| 5,865,807 A * | 2/1999 | Blake, III | 604/167.06 |
| 5,895,377 A | 4/1999 | Smith | |
| 5,899,208 A | 5/1999 | Bonadio | |
| 5,904,703 A | 5/1999 | Gilson | |
| 5,906,577 A | 5/1999 | Beane et al. | |
| 5,947,922 A | 9/1999 | MacLeod | |
| 5,964,781 A | 10/1999 | Mollenauer et al. | |
| 5,989,233 A | 11/1999 | Yoon | |
| 5,993,471 A | 11/1999 | Riza | |
| 5,993,485 A | 11/1999 | Beckers | |
| 5,997,515 A | 12/1999 | de la Torre et al. | |
| 6,010,494 A | 1/2000 | Schafer | |
| 6,024,736 A | 2/2000 | de la Torre et al. | |
| 6,025,067 A | 2/2000 | Fay | |
| 6,033,426 A | 3/2000 | Kaji | |
| 6,033,428 A | 3/2000 | Sardella | |
| 6,045,535 A | 4/2000 | Ben Nun | |
| 6,142,936 A | 11/2000 | Beane et al. | |
| 6,149,642 A | 11/2000 | Gerhart et al. | |
| 6,162,172 A | 12/2000 | Cosgrove et al. | |
| 6,254,533 B1 | 7/2001 | Fadem et al. | |
| 6,254,534 B1 | 7/2001 | Butler et al. | |
| 6,382,211 B1 | 5/2002 | Crook | |
| 6,383,162 B1 | 5/2002 | Sugarbaker | |
| 6,413,244 B1 | 7/2002 | Bestetti | |
| 6,440,063 B1 | 8/2002 | Beane et al. | |
| 6,450,983 B1 | 9/2002 | Rambo | |
| 6,482,181 B1 | 11/2002 | Racenet | |
| 6,485,435 B1 | 11/2002 | Bakal | |
| 6,533,734 B1 | 3/2003 | Corley, III et al. | |
| 6,582,364 B1 | 6/2003 | Butler et al. | |
| 6,589,167 B1 | 7/2003 | Shimomura et al. | |
| 6,589,211 B1 | 7/2003 | MacLeod | |
| 6,613,952 B1 | 9/2003 | Rambo | |
| 6,623,426 B1 | 9/2003 | Bonadio et al. | |
| 6,723,044 B1 | 4/2004 | Pulford et al. | |
| 6,814,078 B1 | 11/2004 | Crook | |
| 6,846,287 B1 | 1/2005 | Bonadio et al. | |
| 6,866,861 B1 | 3/2005 | Luhman | |
| 6,902,541 B1 | 6/2005 | McNally et al. | |
| 6,908,430 B1 | 6/2005 | Caldwell et al. | |
| 6,939,296 B1 | 9/2005 | Ewers et al. | |
| 6,945,932 B1 | 9/2005 | Caldwell et al. | |
| 6,958,037 B1 | 10/2005 | Ewers et al. | |
| 6,972,026 B1 | 12/2005 | Caldwell et al. | |
| 6,997,909 B1 | 2/2006 | Goldberg | |
| 7,052,454 B1 | 5/2006 | Taylor | |
| 2001/0037053 A1 | 11/2001 | Bonadio et al. | |
| 2002/0042607 A1 | 4/2002 | Palmer | |
| 2002/1564322 | 10/2002 | Racenet | |
| 2003/0187376 A1 | 10/2003 | Rambo | |
| 2003/0192553 A1 | 10/2003 | Rambo | |
| 2003/0225392 A1 | 12/2003 | McMichael et al. | |
| 2004/0015185 A1 | 1/2004 | Ewers et al. | |
| 2004/0049100 A1 | 3/2004 | Butler et al. | |
| 2004/0073090 A1 | 4/2004 | Butler et al. | |
| 2004/0092796 A1 | 5/2004 | Butler et al. | |

| | | | | | | |
|---|---|---|---|---|---|---|
| 2004/0106942 | A1* | 6/2004 | Taylor et al. ............... 606/185 | WO | WO0054675 | 9/2000 |
| 2004/0267096 | A1 | 12/2004 | Caldwell et al. | WO | WO01/08581 | 2/2001 |
| 2005/0020884 | A1 | 1/2005 | Hart et al. | WO | WO02/034108 | 5/2002 |
| 2005/0241647 | A1 | 11/2005 | Nguyen et al. | WO | WO03/032819 | 4/2003 |
| 2005/0288558 | A1 | 12/2005 | Ewers et al. | WO | WO03/034908 | 5/2003 |
| 2006/0030755 | A1 | 2/2006 | Ewers et al. | WO | WO03/061480 | 7/2003 |
| 2006/0084842 | A1 | 4/2006 | Hart et al. | WO | WO 2004/075730 A2 | 9/2004 |
| 2006/0149306 | A1 | 7/2006 | Hart et al. | WO | WO 2004/075730 A3 | 9/2004 |

FOREIGN PATENT DOCUMENTS

| | | |
|---|---|---|
| IE | 930649 | 3/1995 |
| IE | 930650 | 3/1995 |
| IE | S950055 | 7/1996 |
| IE | S71634 | 2/1997 |
| IE | S75368 | 8/1997 |
| IE | S970810 | 11/1997 |
| IE | 990219 | 11/2000 |
| IE | 990220 | 11/2000 |
| IE | 990218 | 2/2001 |
| IE | 990660 | 2/2001 |
| IE | 990795 | 3/2001 |
| JP | 02003 235879 A | 8/2003 |
| WO | WO95/07056 | 3/1995 |
| WO | WO95/22289 | 8/1995 |
| WO | WO 95/24864 | 9/1995 |
| WO | WO 95/27468 | 10/1995 |
| WO | WO 99/25268 | 5/1999 |
| WO | WO 00/32116 | 6/2000 |
| WO | WO00/54676 | 9/2000 |
| WO | WO00/54677 | 9/2000 |
| WO | WO 2004/075741 A2 | 9/2004 |
| WO | WO 2004/075741 A3 | 9/2004 |
| WO | WO 2004/075930 A2 | 9/2004 |
| WO | WO 2004/075930 A3 | 9/2004 |
| WO | WO 2005/034766 | 4/2005 |

OTHER PUBLICATIONS

Horigane, et al., Technical Note: Development of a Duodenal Cannula for Sheep, Journal of Animal Science, Apr. 1992, Vol. 70, Issue 4, pp. 1216-1219.

Horigane, et al., Silicone Rumen Cannula with a soft Cylindrical Part and a Hard Flange, Journal of Dairy Science, Nov. 1989, vol. 72, No. 11, pp. 3230-3232.

McSweeney, Cannulation of the Rumen in Cattle and Buffaloes, Australian Veterinary Journal, Aug. 1989, vol. 66, No. 8, pp. 266-268.

Yamazaki et al., Diurnal Changes in the Composition of Abomasal Digesta in Fasted and Fed Sheep, The Tohoku Journal of Agricultural Research, Mar. 1987, vol. 37, No. 3-4, p. 49-58.

Dexterity Surgical, Inc., Dexterity Protractor Instruction Manual.

* cited by examiner

SURGICAL INSTRUMENT ACCESS DEVICE

BACKGROUND OF THE INVENTION

1. Field of the Invention

This invention relates generally to devices and other apparatus facilitating sealed access with surgical instruments across a body wall and into a body cavity.

2. Discussion of the Prior Art

In several areas of surgery there exists a need to have mechanisms or devices that can seal a body cavity or space, and yet permit the introduction of surgical instruments of different sizes such as guidewires, endoscopes and staplers. Typical of these areas of surgery is laparoscopic surgery which relies on surgical instruments inserted through the abdominal wall to reach an operative site within the abdominal cavity. In order to increase space around the operative site within the cavity, insufflation gases are typically introduced to inflate the cavity and elevate the abdominal wall. This pressurizing of the abdominal cavity is referred to as pneumoperitoneum. In this context, the need to seal the body cavity or space arises from the need to maintain the pneumoperitoneum even when the instruments are present.

Trocars have been commonly used to provide instrument access in laparoscopic surgeries. These trocars have included elaborate seal structures having zero seals which prevent escape of the gases in the absence of instruments, and instrument seals which prevent escape of the gases in the presence of instruments. Unfortunately, the instrument seals have been able to accommodate only a narrow range of instrument diameters. Where wider ranges were desired multiple seal pairs had to be provided.

Some instruments such as surgical staplers and those having diameters up to about 37 mm have been too large for trocar access. Furthermore, present trocar seals typically require two valves, one for forming an instrument seal in the presence of the instrument, and the other for forming a zero seal in the absence of the instrument. Accordingly, there is a need in the art for a surgical access device that can function both as a zero seal and as an instrument seal, and that can accommodate a wide range of instruments having diameters up to about 37 mm.

SUMMARY OF THE INVENTION

The deficiencies of the prior art are overcome with the present invention which includes a seal apparatus. In one embodiment, the device includes a valve structure formed of a gel including, for example, a thermoplastic base such as KRATON® and an oil. The resulting elastomer has excellent tear strength, high elongation, a very low durometer or hardness, and biocompatibility. The access device can function both as a zero seal and as an instrument seal. Furthermore, it can accommodate a full range of instruments having diameters up to about 37 mm. In another embodiment, several instruments of smaller diameter can be accommodated at the same time with a single access device.

Both tear resistance and sealing capability can be enhanced by encapsulating the gel in a sheath or otherwise providing circumferential reinforcement for the valve structure. Additives can be provided either on or in the gel to enhance properties such as lubricity, appearance, wound treatment and/or protection, anti-cancer protection and antimicrobial protection. Additional chemicals, compounds, pharmaceuticals or even mechanical devices can be mixed with or embedded in the gel material to vary chemical, pharmaceutical or physical properties of the access device.

These and other features and advantages of the invention will be clarified with a description of preferred embodiments and reference to the associated drawings.

DESCRIPTION OF PREFERRED EMBODIMENTS AND BEST MODE OF THE INVENTION

Figure 1:
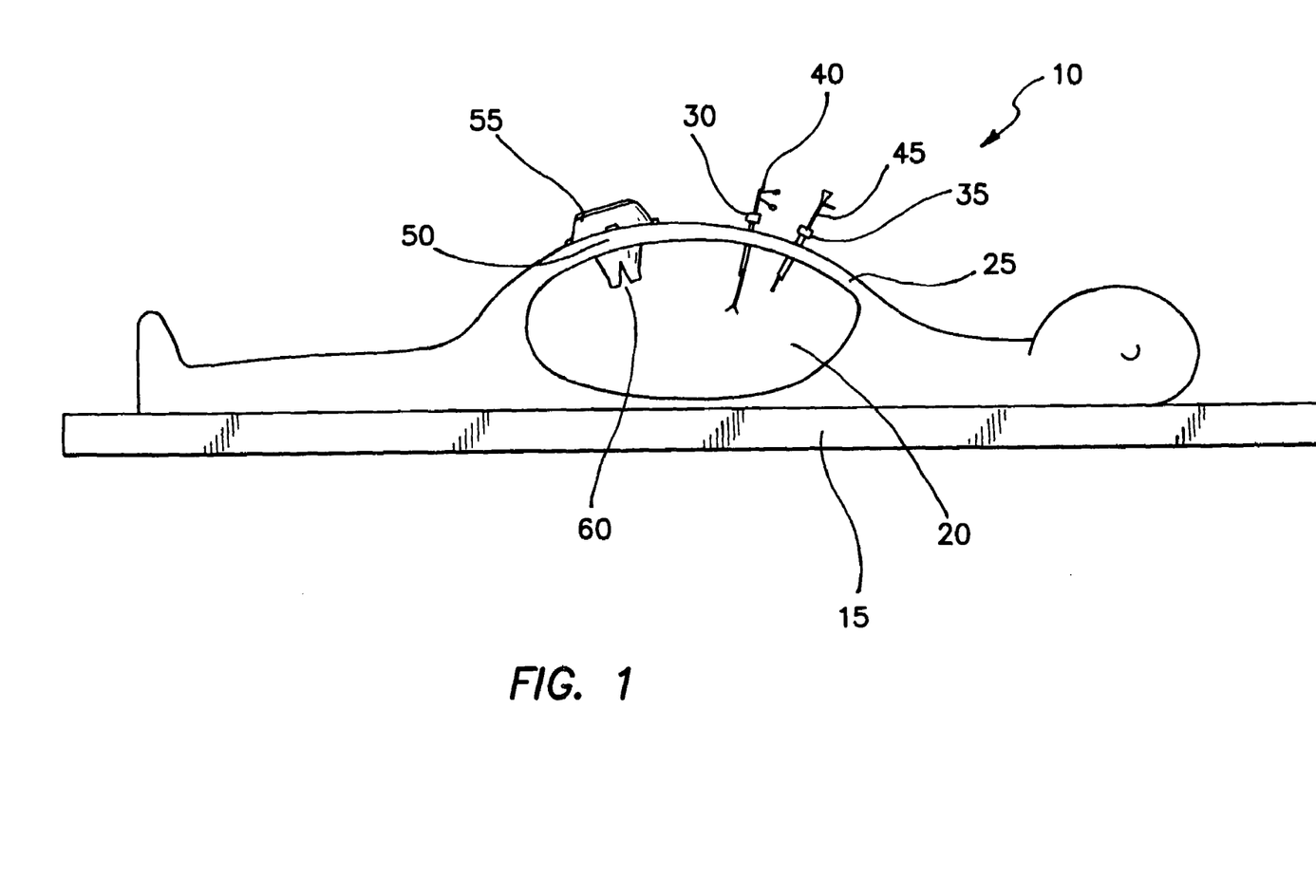
FIG. 1 is a perspective view showing a patient prone on an operating table with his abdomen insufflated, and with instrument access provided by trocars and the access device of the present invention.

A patient is illustrated in FIG. 1 and designated generally by the reference numeral 10. The patient 10 is shown in a prone position on an operating table 15, where the operative procedure is performed within an abdominal cavity 20 with instrument access provided through an abdominal wall 25. In this type of operation, commonly referred to as laparoscopic surgery, trocars 30 and 35 are commonly used to provide minimally invasive access through the abdominal wall 25 for instruments such as a grasper 40 and an endoscope 45.

Although the specific focus of this disclosure will be on a preferred laparoscopic procedure, it will be noted that laparoscopic surgery is merely representative of a type of operation wherein a procedure can be performed in a body cavity with minimal access through a body wall.

Notwithstanding the foregoing generality, it is important to note that with respect to laparoscopic surgery, it is often desirable that instruments having diameters up to 37 mm be able to insert through the abdominal wall 25 and into the abdominal cavity 20 using the same access device. This insertion of the instruments provides a surgeon with direct access to various elements of the anatomy without having to change access device or use of multiple access devices.

In order to accommodate a wide range of instruments, a small incision 50 is typically created in the abdominal wall 25. An access device 55 of the present invention can be provided to further facilitate insertion of wide instruments such as those having diameters up to about 37 mm.

Particularly in the case of laparoscopic surgery, it is advantageous to insufflate the abdominal cavity 20 with a gas, such as carbon dioxide, in order to elevate the abdominal wall 25 and thereby increase the volume of the working space within the cavity 20. Maintenance of this insufflation pressure, commonly referred to as pneumoperitoneum, is particularly difficult where access is desired across the abdominal wall 25, for example, through the trocars 30, 35, as well as the access device 55. For this reason, a substantial effort has been directed to providing such access devices with sealing characteristics both in the presence of instruments and in the absence of instruments, such as the grasper 40 and scope 45.

Were it not for the desire to maintain the pneumoperitoneum, there would be no need for the trocars 30, 35 or the access device 55. One would merely cut an incision in the abdominal wall 25 and insert the instrument directly through the incision. However, without appropriate valves or seals, the insufflation gases would merely escape through the incisions. This would be particularly detrimental in the case of the incision 50 which must be sufficiently large to accept the wide range of instruments having diameters up to 37 mm. Thus, it is a primary purpose of the access device 55 to form with the incision 50 an access or working channel 60, and to provide a valve or other sealing structure across the working channel 60 in order to maintain the pneumoperitoneum.

Figure 2:
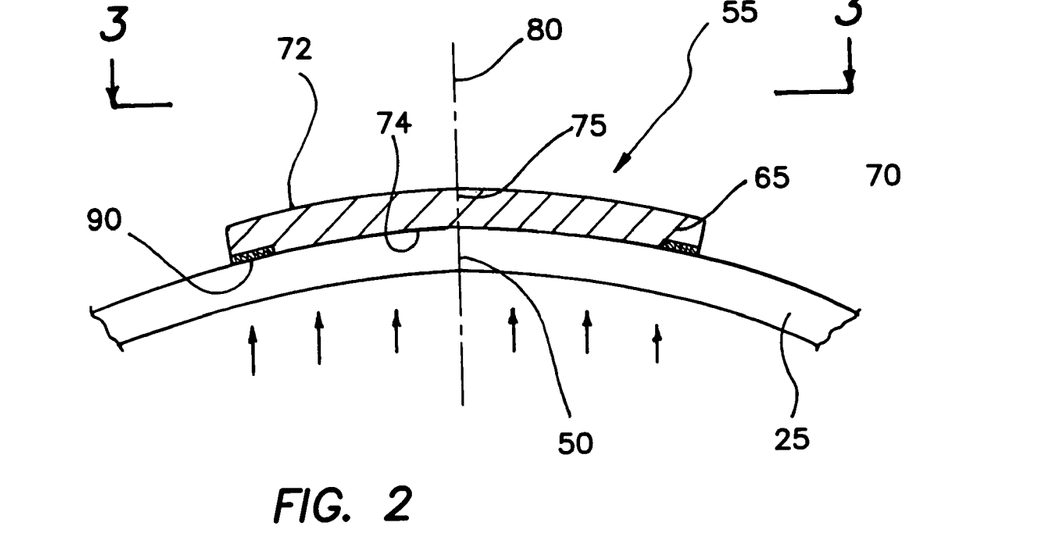
FIG. 2 is an enlarged side elevation view of the access device operatively disposed exteriorly of the abdominal wall.

An enlarged view of one embodiment of the access device 55 is illustrated in FIG. 2, which also shows the abdominal wall 25 and the incision 50. In this simple form, the access device 55 has the general configuration of a pad 65, meaning that it is generally flat and disposed in a plane such as the plane 70. Typically parallel to this plane 70 are a pair of major surfaces of 72 and 74 which provide the pad 65 with a substantial surface area. An opening or slit 75 can be formed through the pad 65, generally along an axis 80 perpendicular to the plane 70.

When operatively disposed, the opening 75 of the pad 65 is in communication with the incision 50 and, in this case, forms with the incision 50 and the working channel 60. The alignment of the opening 75 and incision 50 can occur with the pad 65 disposed exteriorly of the abdominal wall as illustrated in FIG. 2. The operative disposition of the pad 65 relative to the abdominal wall 25 requires that the pad 65 be maintained in its operative position and that it form a seal around the incision 50. Referring to the plan view of FIG. 3, these two functions are accomplished with an adhesive 85 disposed around the incision 50 between the pad 65 and the abdominal wall 25.

Figure 3:
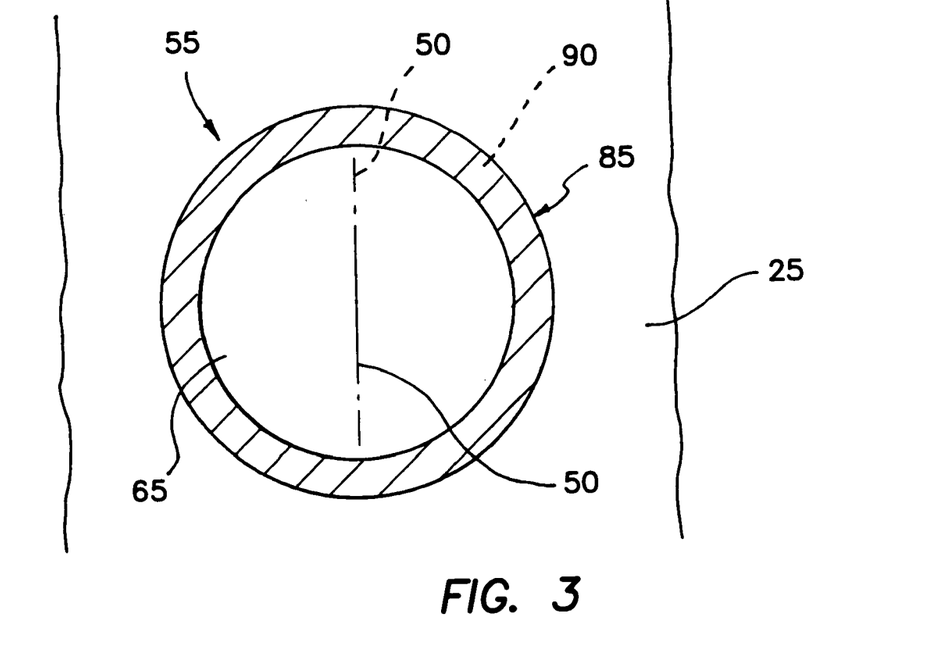
FIG. 3 is a plan view taken along lines 5—5 of FIG. 2.

If this adhesive 85 is formed as a continuous ring 90, as illustrated in FIG. 3, the pad 65 can be disposed with the ring 90 positioned circumferentially around the incision 50 to form a seal between the pad 65 and the abdominal wall 25. In the illustrated example, when the pad 65 is operatively positioned, the escape of insufflation gases is inhibited between the pad 65 and the abdominal wall 25 by the adhesive ring 90.

The escape of insufflation gases is inhibited through the opening 75 of the pad 65 by the self-sealing characteristics of the material forming the pad 65. This material of the pad 65 and its highly advantageous properties are discussed below.

It will be appreciated that the functions of the adhesive ring 90 can be accomplished in many different ways using many different materials and shapes. For example, many materials other than adhesives can be used to maintain the pad 65 in position over the incision 50. The formation of a seal around the incision 50 can also be accomplished with methods other than adhesion. Furthermore, the shape of the continuous seal formed by the adhesive 85 need not be in the shape of a circle. Rather, any continuous pattern sufficiently large to form a perimeter around the incision 50 could facilitate the desired sealing relationship.

It will be noted that whenever an instrument is inserted through the pad 65, the material of the pad conforms to the surface of the instrument and forms the instrument seal with the instrument. Accordingly, during the entire period beginning with insertion of the instrument and ending with withdrawal of the instrument, there is substantially no loss of insufflation gas through the pad 65 or any loss of pneumoperitoneum within the abdominal cavity 20.

It will be appreciated an instrument having a diameter up to 37 mm may be inserted through the access device 55 of the invention. In the absence of the instrument, the opening or slit 75 merely closes against itself to form a zero seal, thus preventing the escape of insufflation gases through the access device 55. When the instrument is inserted through the opening or slit 75, an instrument seal is formed between the material of the access device 55 and the exterior surface of the instrument. This prevents the escape of insufflation gases through the access device 55, even when an instrument is present. Thus, insufflation pressures can be maintained within the abdominal cavity 20 whether or not the instrument is in place. Note that these seals, the zero seal and the abdominal seal, can be formed as a single valve structure having properties for accommodating a full range of instrument sizes up to 37 mm in diameter.

In most cases, the single access opening 75 is used to accommodate a single instrument. It is appreciated, however, that the access device 55 can also accommodate multiple instruments of smaller diameters. That is, additional openings may be established by merely inserting the desired operative instrument through the pad 65. In this manner, the instrument can create its own access hole beside the primary opening 75. Particularly for those operative instruments having pointed distal ends, the instrument can merely be forced through the pad 65 forming its own access hole, such as the opening 75, as it is moved distally. This opening, created by the operative instrument itself, would automatically form an instrument seal as the instrument is inserted, as well as a zero seal as the instrument is withdrawn.

For operative instruments not having pointed distal ends, it is possible to form a new access hole using a secondary instrument, such as a trocar obturator. After the access hole is formed, the obturator can be removed, vacating the access hole to receive the operative instrument. Throughout this process of initially forming an access hole and ultimately inserting an operative instrument through the hole, both zero seals and instrument seals are formed to maintain the pneumoperitoneum.

With the advantages associated with (1) the formation of an instrument seal and a zero seal with a single valve accommodating a wide range of diameters, and (2) the formation of an instrument opening using the instrument itself, it will be appreciated that the concept of this invention will typically be embodied with a structure that is particularly dependent upon the material which forms the access device 55. In a preferred embodiment, the pad 65 is formed of a KRATON®/oil mixture including a KRATON® Triblock with a Styrene-Ethylene-Butylene-Styrene (S-E-B-S) structure in combination with a mineral oil.

As described in co-pending U.S. application Ser. No. 10/381,220, filed on Mar. 20, 2003, entitled "Surgical Access Apparatus and Method," which is fully incorporated herein by reference, it can be appreciated that an almost infinite number of combinations, alloys, and Styrene to rubber ratios can be formulated, each capable of providing advantages to a particular embodiment of the invention. These advantages will typically include low durometer, high elongation, and good tear strength.

Figure 4:
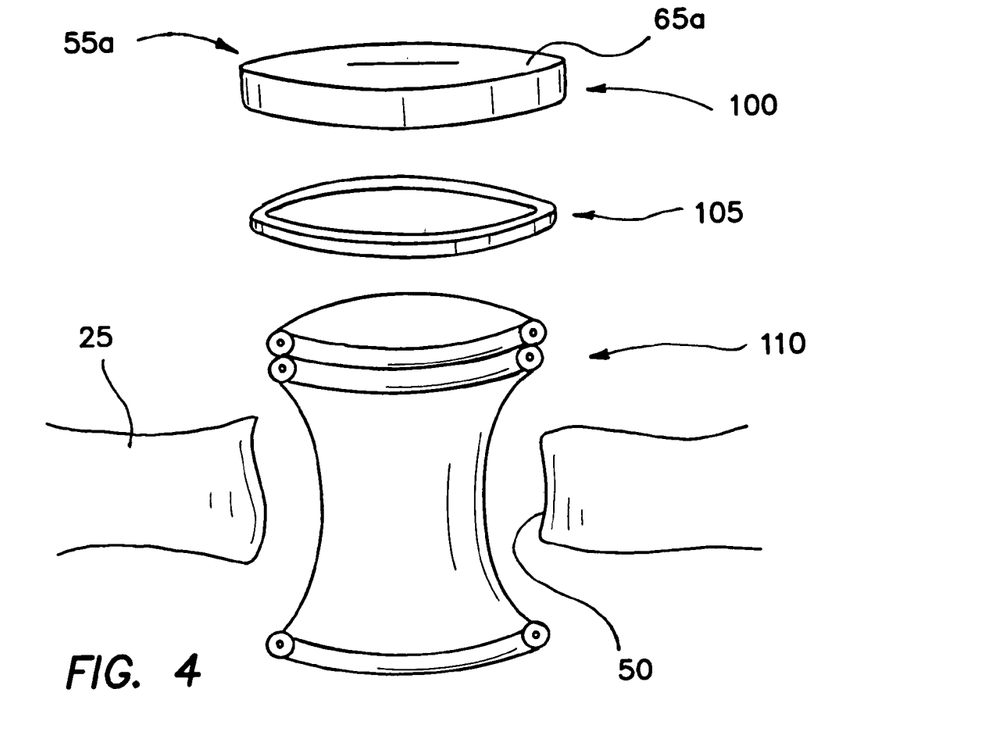
FIG. 4 is a perspective exploded view of a further embodiment including a gel cap, a base and a wound retractor.

A further embodiment of the invention is illustrated in FIG. 4 where elements of structure similar to those previously disclosed are designated with the same reference numeral followed by the lower case letter "a." This exploded view of the access device 55a includes not only the pad 65a but also a complimentary structure for maintaining the position of the pad 65a, for forming a seal between the pad 65a and the abdominal wall 25, and for dilating the incision 50 to a variable extent as required by a surgeon. In this case, the access device 55a includes three components, a jell cap 100, base 105, and a wound retractor 110 as described in co-pending International Application No. PCT/US03/17389, filed on Jun. 3, 2003, entitled "Wound Retractor," which is fully incorporated herein by reference.

Figure 6:
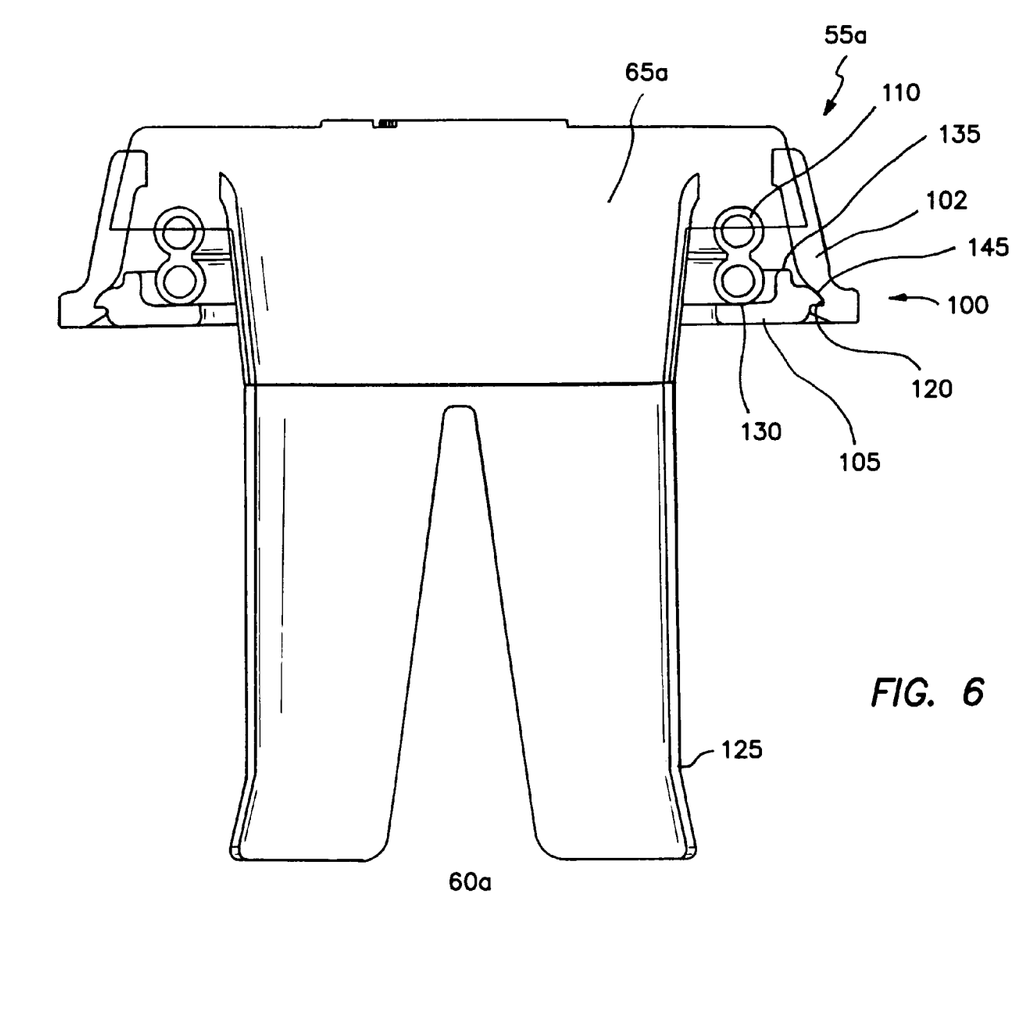
FIG. 6 is a cross-section view of an access device of the invention including a gel cap, a base, a wound retractor, and a protective sleeve formed around an inner diameter of a cap ring of the gel cap.
Figure 7:
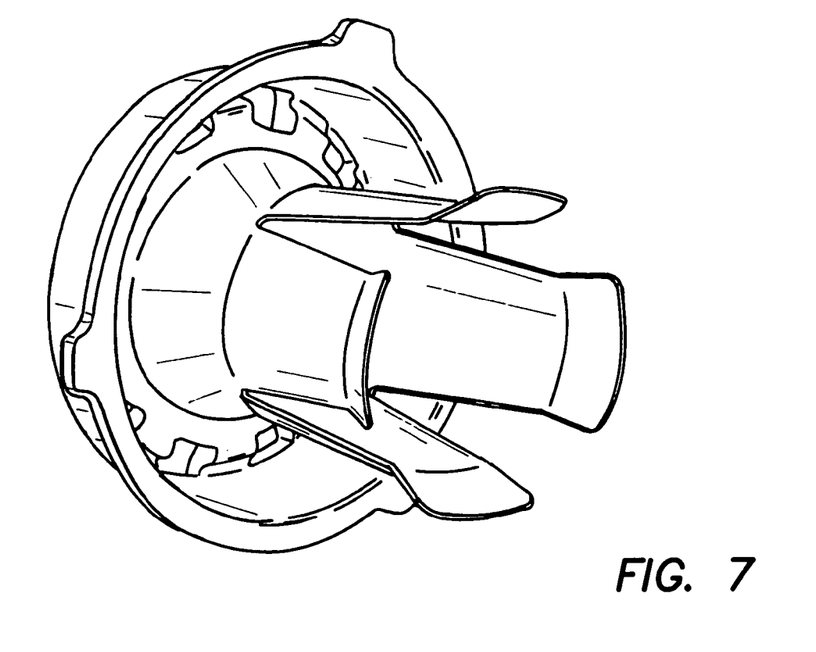
FIG. 7 is a three-dimensional view of the protective sleeve formed around the inner diameter of the cap ring of the access device of the invention.
Figure 8:
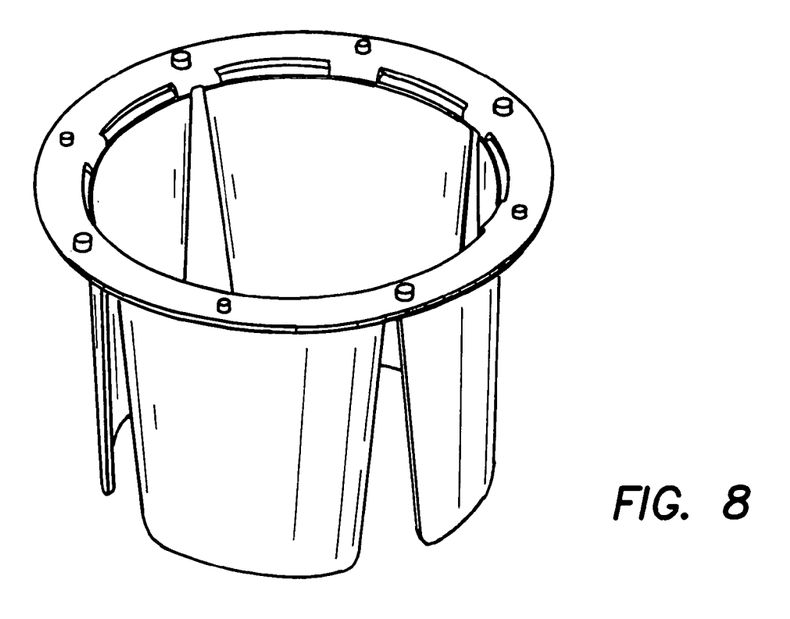
FIG. 8 is a three-dimensional view of a protective sleeve formed around an inner diameter of a cap ring of an access device in accordance to another embodiment of the invention.

Referring to FIG. 6, there is shown a cross-sectional view of the access device 55a, with the gel cap 100 and the base 105 attached together and the wound retractor 110 held therein. The gel cap 100 further includes a circumferential cap ring 102, which can be inserted and molded to the pad 65a, and a protective shield or sleeve 125, which can be bonded or molded into cap 100. The shield or sleeve 125 is positioned under pad 65a and circumferentially around an inner diameter of cap ring 102, and is directed into the incision 50. The shield or sleeve 125 operates to protect the sheath of wound retractor 110 from sharp instruments as the instruments are inserted and withdrawn through the pad 65a; the shield 125 also operates to direct instruments through the pad 65a. The shield 125 may be a single tubular member or it may comprise a plurality of axially extending sleeve members having a plurality of axial slits as illustrated in FIGS. 7 and 8. The shield 125 may comprise of the same or different materials as the cap ring 102. The resulting gel cap 100 forms a seal with the base 105, thereby defining a working channel 60a through the pad 65a, the cap ring 102, the base 105, and the wound retractor 110. In the manner previously discussed, this working channel 60a includes the single valve formed by the gel pad 65a which provides both a zero seal and an instrument seal for a wide range of instrument diameters.

Figure 5:
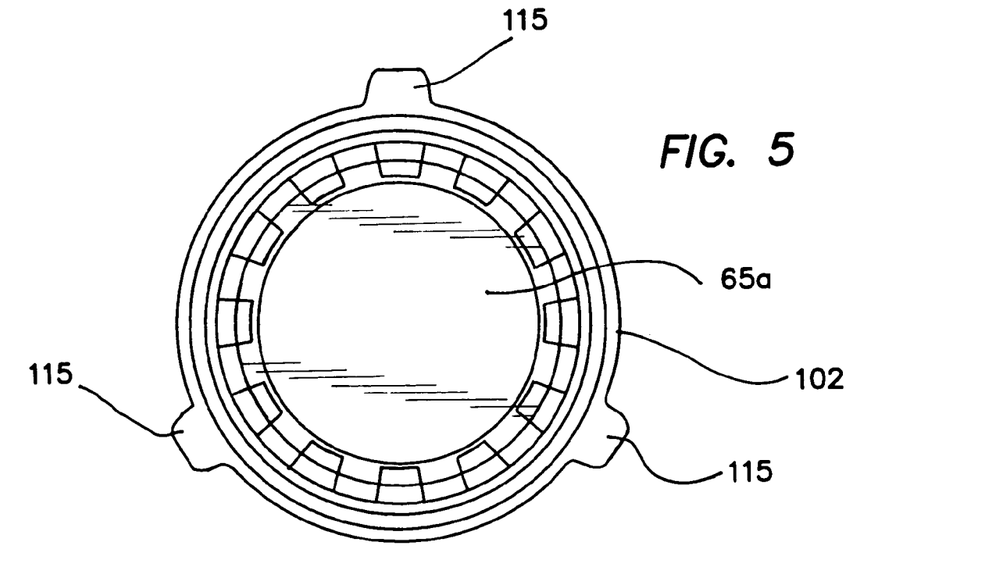
FIG. 5 is a top plan view of a gel cap of an access device of the invention.

The structure associated with the gel cap 100 is described in greater detail with reference to FIG. 5. In the top plan view of FIG. 5, it can be seen that this embodiment includes the gel pad 65a centrally disposed within the circumferential cap ring 102. Holding tabs 115 can be provided to extend radially outwardly of the cap ring 102. These holding tabs 115 can facilitate the sealing engagement of the gel cap 100 with the base 105 in the manner described in greater detail below.

The gel pad 65a can be formed of any of the materials previously discussed although the preferred embodiment includes the KRATON®/mineral oil gel. The cap ring 102 for such an embodiment can be advantageously formed of KRATON® only. This will make the cap ring 102 more rigid than the gel pad 65a while maintaining an excellent material interface between the pad 65a and the ring 102. In a typical manufacturing operation, the cap ring 102 will be predisposed in the mold for the gel pad 65a with the unitary structure of the gel cap 100 resulting.

Figure 9:
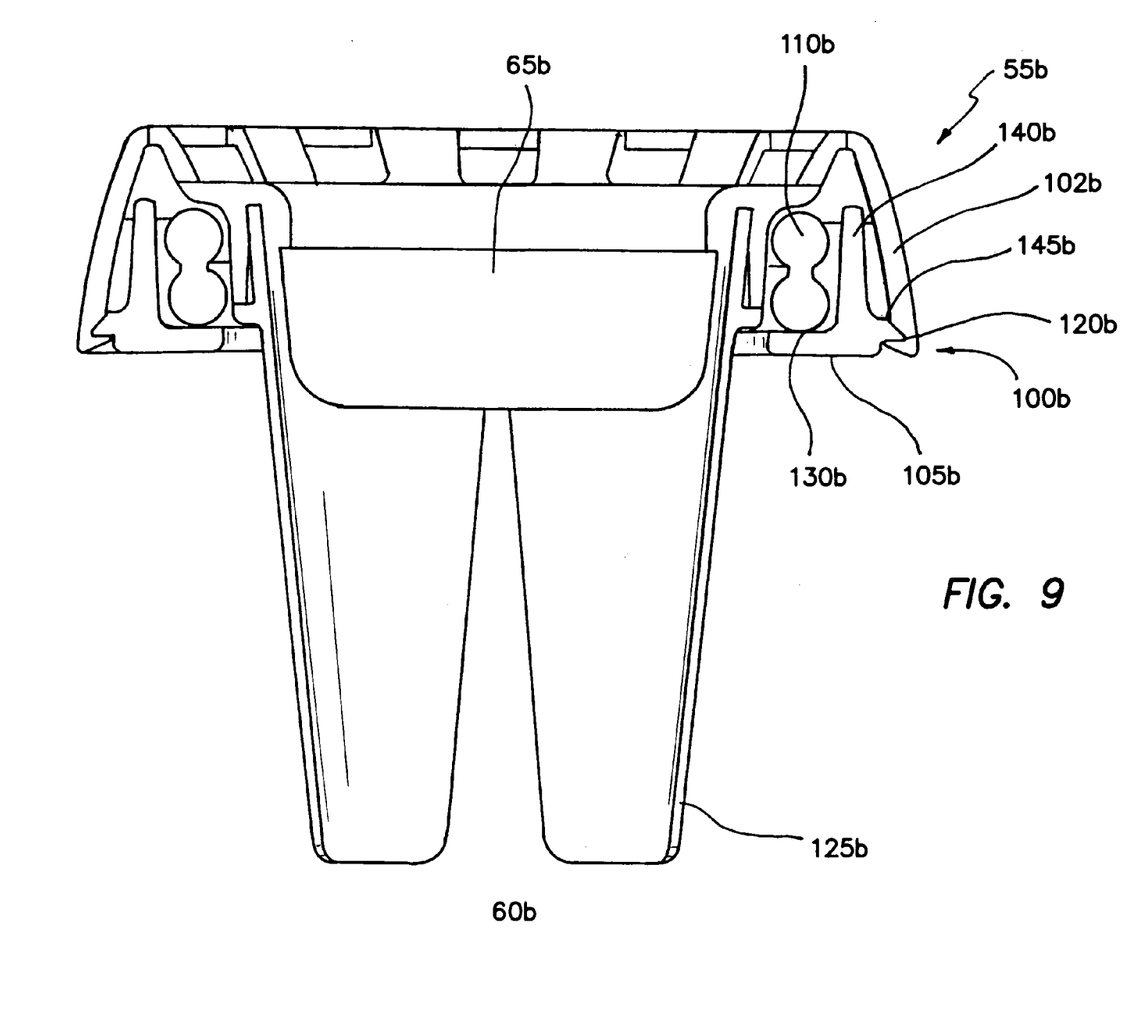
FIG. 9 is a cross-section view of an access device in accordance with another embodiment of the invention including a gel cap, a base, a wound retractor, and a protective sleeve formed around an inner diameter of a cap ring of the gel cap.
Figure 10:
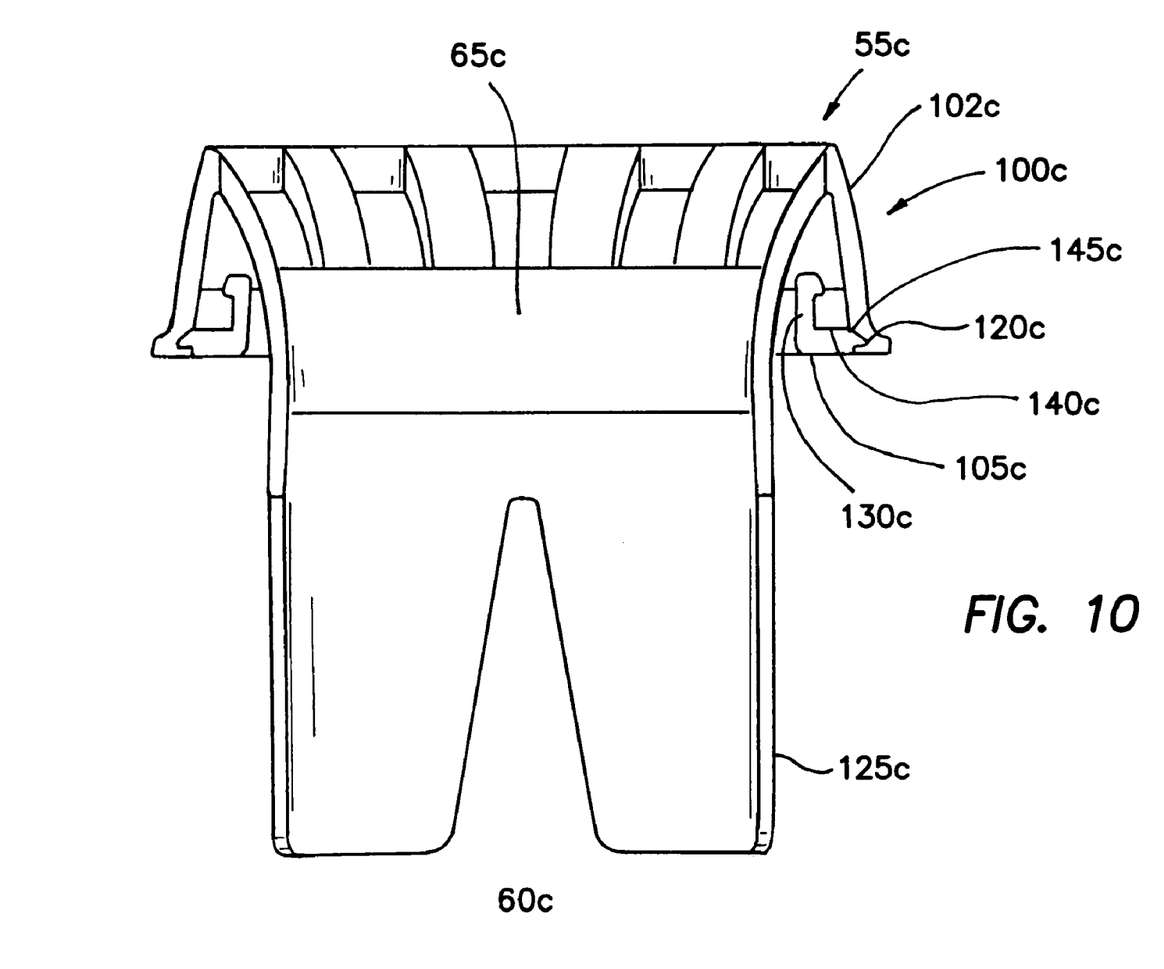
FIG. 10 is a cross-section view of an access device in accordance with another embodiment of the invention including a gel cap, a base, a wound retractor (not shown), and a protective sleeve formed around an inner diameter of a cap ring of the gel cap.

The cross-section view of FIG. 6 further illustrates an annular void 120 formed on the inner circumference of the cap ring 102. This void 120 is of particular advantage in forming a sealing relationship with the base 105 in the manner discussed in greater detail below. FIGS. 9 and 10 illustrate additional exemplary embodiments of the invention having modifications that could be made to the gel cap 100 and/or the base 105 so that the access device 55 can be used with the wound retractor 110. Referring back to FIG. 6, it will be noted that the base 105 can be provided with a generally straight inner surface 130 which extends distally to a rounded end surface 135 and outwardly from the end surface 135 along an annular lip 145, which is sized and configured to fit into the annular void 120 formed on the inner circumference of cap ring 102.

In another embodiment of the invention, FIG. 9 illustrates a base 105b having a generally straight inner surface 130b which extends distally to a raised wall 140b and outwardly from the raised wall 140b along an annular lip 145b, which is sized and configured to fit into an annular void 120b formed on the inner circumference of a corresponding cap ring 120b. In yet another embodiment of the invention, FIG. 10 illustrates a base 105c having a raised wall 130c along an inner diameter and a generally straight surface 140c extending distally along an annular lip 145c, which is sized and configured to fit into an annular void 120c formed on the inner circumference of a corresponding cap ring 120c.

Figure 11:
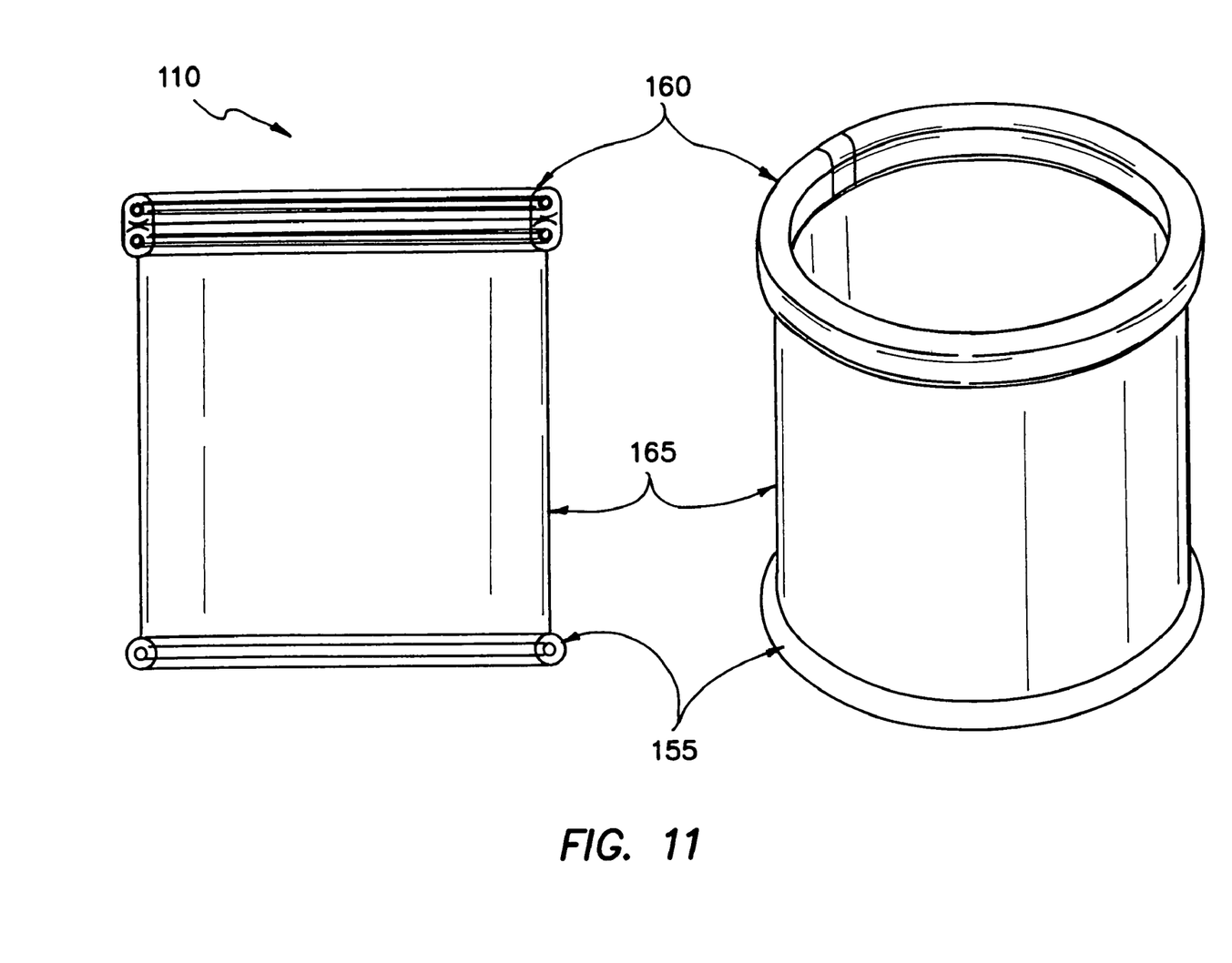
FIG. 11 illustrates a cross-section view and a three-dimensional view of the wound retractor of an access device of the invention including an inner ring, an outer ring, and a flexible sleeve.

Referring to FIG. 11, there is shown the incrementally adjustable wound retractor 110 of the invention which operates to seal edges of a surgical incision and forms an opening in a patient's body cavity. The wound retractor 110 comprises an inner ring 155, an outer ring 160, and a flexible sleeve 165 connecting the inner ring 155 and the outer ring 160. The wound retractor 110 provides a path for a surgeon to insert instruments through the opening formed by the wound retractor 110. The wound retractor 110 is incrementally adjustable to fit a wide range of incision sizes. The wound retractor 110 is installed or placed in a body cavity such that the inner and outer rings 155, 160 expand around inner and outer edges of the incision. Any portion of the flexible sleeve 165 extending outside the incision can be easily rolled onto the outer ring 160 to tightly seal the sides of the wound. The outer ring 160 is preferably shaped to provide audible and/or tactile feedback to the user. The outer ring 160 includes surfaces that are easy to grip and turn to allow the user to manually turn the outer ring 160 and roll up the flexible sleeve 165 with ease. The outer ring 160 may be solid or include a single or multiple lumen(s) with rod(s) placed therein to provide audible signal to the user as the outer ring 160 is turned.

Figure 12:
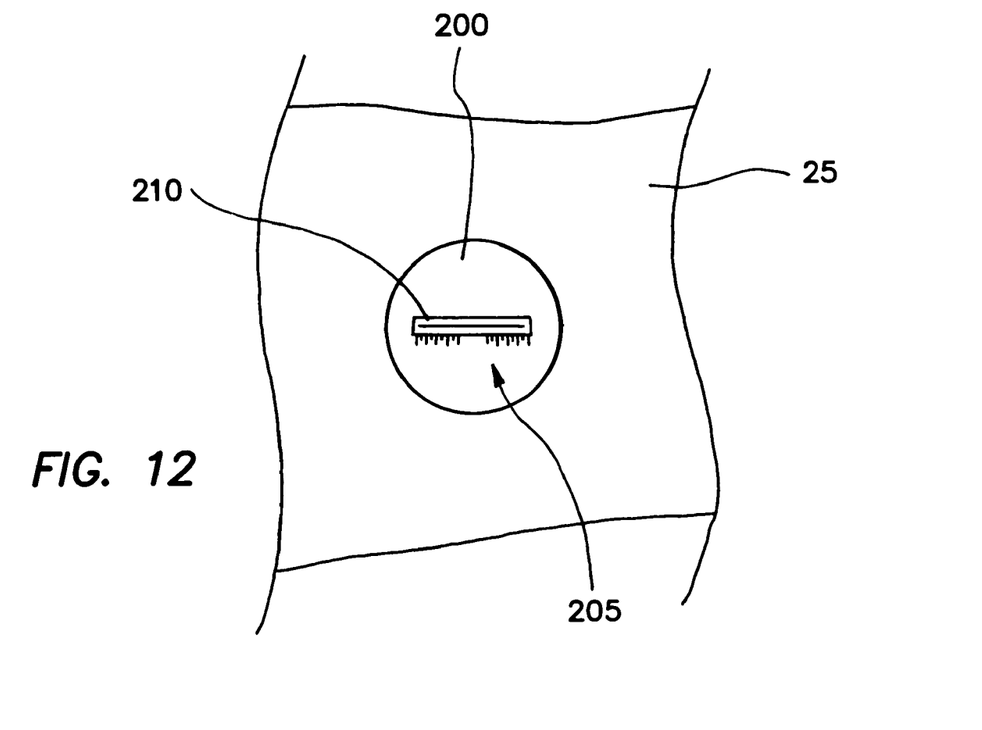
FIG. 12 is a top plan view showing use of a template.
Figure 13:
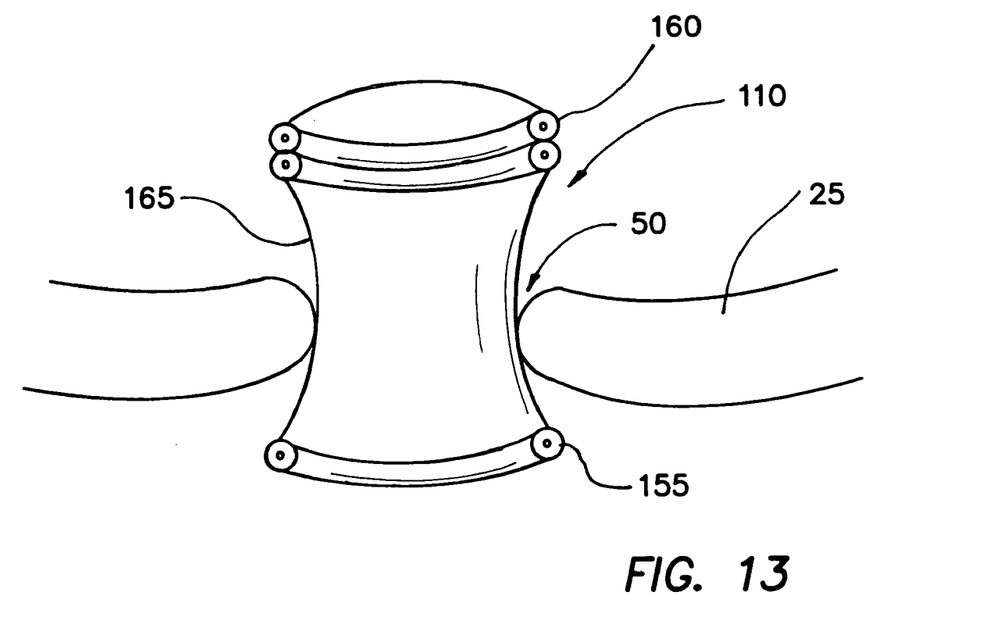
FIG. 13 is an axial cross-section view showing placement of the inner ring and securement of the flexible sleeve of the wound retractor of the invention.

The method of using the access device of the present invention is illustrated in the progressive use of FIGS. 12 and 13. In FIG. 12, a top plan view of the abdominal wall 25 of the patient 10 is illustrated with a template 200 positioned to facilitate location of the incision 50. The size of the incision 50 can be determined with the indicia 205 on the template 200 showing the lengths of the incision. After the incision 50 has been cut along the line 210, the template 200 can be removed. As illustrated in FIG. 13, the wound retractor 110 can then be mounted through the incision 50. Initially the inner ring 155 is compressed and fed through the incision 50. On the inner surface of the abdominal wall 25, the inner ring 155 is free to expand to its larger diameter. Any portion of the flexible sleeve 165 extending outside the incision 50 can be easily rolled onto the outer ring 160 to tightly seal the sides of the wound. As noted, when the sleeve 165 is axially stretched, it will create radial forces on the abdominal wall 25 which will tend to enlarge the incision 50. The greater the axial stretch, the larger the incision 50.

A final step remaining in this process is the attachment of the gel cap 100 to the base 105. This is accomplished as illustrated in FIGS. 6, 9 and 10 by capturing the annular lip 145 of the base 105 in the annular void 120 of the gel cap 100. Bending the holding tabs 115 upwardly and outwardly facilitates this engagement which ultimately forms a seal between the base 105 and the gel cap 100.

Although this invention has been disclosed with reference to certain structural configurations, it will be appreciated that these products are merely representative of many different embodiments of the invention. Accordingly, one is cautioned not to limit the concept only to the disclosed embodiments, but rather encouraged to determine the scope of the invention only with reference to the following claims.

The invention claimed is:

1. A surgical access device facilitating a sealing relationship with an instrument extending through the device and into an incision in a body wall of a patient, the access device comprising:
   a valve structure disposed relative to the incision in a sealing relationship with the body wall around the incision and extending into communication with the incision in the patient;
   a cap ring inserted or molded into the valve structure;
   a wound retractor adapted to dilate the incision;
   a protective sleeve extending into communication with the incision, the protective sleeve being bonded or molded around an inner diameter of the cap ring;
   a single seal included in the valve structure and disposed relative to the incision in the body wall;
   the single seal having a first state in the absence of an instrument extending through the valve structure, and a second state in the presence of an instrument extending through the valve structure;
   the single seal in the first state forming a zero seal in the absence of the instrument extending through the valve structure; and
   the single seal in the second state forming a seal with the instrument in the presence of the instrument extending through the access device.

2. The surgical access device of claim 1, wherein the protective sleeve provides for wound protection during insertion and withdrawal of the instrument.

3. The surgical access device of claim 1, wherein the protective sleeve is a single tubular member.

4. The surgical access device of claim 1, wherein the protective sleeve comprises a plurality of axially extending sleeve members having a plurality of axial slits.

5. A surgical access device facilitating a sealing relationship with an instrument extending through the device and into an incision in a body wall of a patient, the access device comprising:
   a valve structure disposed relative to the incision in a sealing relationship with the body wall around the incision and extending into communication with the incision in the patient;
   a cap ring inserted or molded into the valve structure;
   at least one support ring disposed circumferentially of the valve structure forming a hollow space,
   a wound retractor adapted to dilate the incision, the wound retractor being operatively placed in the hollow space;
   a protective sleeve extending into communication with the incision, the protective sleeve being bonded or molded around an inner diameter of the cap ring;
   a single seal included in the valve structure and disposed relative to the incision in the body wall;
   the single seal having a first state in the absence of an instrument extending through the valve structure, and a second state in the presence of an instrument extending through the valve structure;
   the single seal in the first state forming a zero seal in the absence of the instrument extending through the valve structure; and
   the single seal in the second state forming a seal with the instrument in the presence of the instrument extending through the access device.

6. The surgical access device of claim 5, wherein the wound retractor includes an inner ring, an outer ring, and a flexible sleeve connecting the inner ring and the outer ring.

7. A low-profile surgical valve structure adapted for disposition relative to an incision in a body wall and proximate an outer surface of the body wall, the incision being retracted by an incrementally adjustable wound retractor having an inner ring, an outer ring, and a flexible sleeve connecting the inner ring to the outer ring, the inner ring expanding around an inner edge of the incision, the outer ring expanding around an outer edge of the incision, portions of the flexible sleeve extending outside the incision being rolled around the outer sleeve to retract the incision, thereby forming a channel through the body wall and into a body cavity, the valve structure facilitating insertion of a surgical instrument through the valve structure and maintenance of a sealing relationship with the surgical instrument, comprising:
   a gel pad adapted to be disposed over the incision and forming a seal with the wound retractor, the gel pad including a gel material comprising Styrene-Ethylene/Butylene-Styrene block copolymer and oil, and a slit formed in the pad to provide an access opening through the pad, the slit being adapted to extend into communication with the incision; and
   a circumferential cap ring molded to the gel pad, the cap ring being adapted to removably couple the valve structure to the outer ring of the wound retractor,
   wherein the access channel forms a zero seal in the absence of an instrument extending therethrough and an instrument seal in the presence of an instrument extending therethrough.

8. The valve structure of claim 7, the cap ring forming a hollow space adapted to receive the wound retractor.

9. The valve structure of claim 7, wherein the gel pad includes a single access opening.

10. The valve structure of claim 7, further comprising at least one additional access opening in the gel pad, the at least one additional access opening being formed by inserting an instrument through the gel pad away from the slit.

* * * * *